United States Patent
Meignant et al.

(10) Patent No.: US 6,610,325 B1
(45) Date of Patent: Aug. 26, 2003

(54) TABLETS TO BE CRUNCHED OR SUCKED, COMPRISING IRON AS ACTIVE PRINCIPLE

(75) Inventors: Catherine Meignant, Paris (FR); Stephanie Verdier, Paris (FR)

(73) Assignee: Laboratoire Innothera, Arcueil (FR)

( * ) Notice: Subject to any disclaimer, the term of this patent is extended or adjusted under 35 U.S.C. 154(b) by 0 days.

(21) Appl. No.: 09/600,169

(22) PCT Filed: Nov. 18, 1998

(86) PCT No.: PCT/FR98/02462
§ 371 (c)(1),
(2), (4) Date: Oct. 23, 2000

(87) PCT Pub. No.: WO99/39708
PCT Pub. Date: Aug. 12, 1999

(30) Foreign Application Priority Data

Feb. 3, 1998 (FR) .............................................. 98 01223

(51) Int. Cl.$^7$ ................................................ A61K 9/20
(52) U.S. Cl. ...................... 424/464; 424/439; 424/440; 424/441; 424/465; 514/974
(58) Field of Search ................................ 424/464, 465, 424/441, 440, 439, 435

(56) References Cited

U.S. PATENT DOCUMENTS 5,174,987 A * 12/1992 Takaichi et al. ................ 424/9
5,409,905 A   4/1995 Eby, III ........................ 514/23

FOREIGN PATENT DOCUMENTS

| EP | 0737473 | 10/1996 | |
| GB | 2195890 | 4/1988 | |
| GB | 2195891 | 4/1988 | |
| SU | 1644879 A | * 4/1991 | ............ A23K/1/20 |

* cited by examiner

*Primary Examiner*—James M. Spear
(74) *Attorney, Agent, or Firm*—Jacobson Holman PLLC

(57) ABSTRACT

This pharmaceutical medicine comprises an iron salt, not less than two polyols, a binding agent, a lubricating agent, and a flavoring agent. The dose of elemental iron is not less than 5 mg, and preferably 10 mg to 15 mg per tablet. The proportion of one of the polyols on its own is not less than 10%, and preferably not less than 20% of the total mass of the tablet, the overall proportion of the polyols being not less than 50% and preferably not less than 75%. One of the two polyols is xylitol, comprising not less than 10%, and preferably not less than 20%. The other polyol is sorbitol and/or mannitol.

19 Claims, No Drawings

TABLETS TO BE CRUNCHED OR SUCKED, COMPRISING IRON AS ACTIVE PRINCIPLE

This application is a 371 of PCT/FR98/02462 filed Nov. 18. 1998.

The invention relates to a pharmaceutical medicine in unit galenical formulation for chewing or sucking and including elemental iron as its active principle.

Such a medicine is indicated in preventing or correcting conditions associated with a shortage of iron or with an iron imbalance. These troubles are treated by supplying elemental iron in the form of ferrous salts ($Fe^{2+}$) or ferric salts ($Fe^{3+}$), although ferric salts are less used.

When these iron salts are administered per os, a difficulty lies in the taste being disagreeable when in doses sufficient to obtain the desired therapeutic effects, i.e. doses of the order of several milligrams or several tens of milligrams per tablet (ignoring the specific case of multiple food additives and other mineral or vitamin supplements having an iron content that is very low and therefore of no effect on taste).

That is why medicines containing an iron salt as active principle are generally presented in the form of a tablet that is coated (sugar-coated) or provided with a skin so that the problem of the disagreeable taste of iron salts does not arise for such medicines.

One of the objects of the present invention is to propose a particular formulation of a medicine containing an iron salt making a tablet for chewing or sucking, which formulation is galenically acceptable, industrially manufacturable, stable, and above all of acceptable taste.

To this end, the medicine of the invention comprises an iron salt, not less than two polyols, a binding agent, a lubricating agent, and a flavoring agent.

According to various advantageous subsidiary characteristics:

- the proportion of one of the polyols on its own is not less than 10%, and preferably not less than 20% of the total mass of the tablet, and the overall proportion of the polyols is not less than 50%, preferably not less than 75%, of the total mass of the tablet;
- one of the two polyols is xylitol, comprising not less than 10%, and preferably not less than 20% of the total mass of the tablet;
- the medicine optionally comprises three polyols, where the polyol other than xylitol is sorbitol and/or mannitol;
- the binding agent is microcrystalline cellulose;
- the lubricating agent is selected from the group comprising micronized stearic acid, talc, and mixtures thereof;
- the iron salt is either a ferrous salt such as iron sulfate, iron succinate, iron gluconate, iron glycerophosphate, iron glucoheptonate, iron dl-aspartate, iron fumarate, iron pyrophosphate, and iron oxide, or else a ferric salt such as ferric ammonium citrate, ferric chloride, ferric citrate, ferric pyrophosphate, and ferric edetate; the dose of iron is not less than 5 mg, and preferably 10 mg to 40 mg of elemental iron per tablet; and
- the general formula of the medicine is: ferrous sulfate: quantity corresponding to elemental iron: 5 mg to 15 mg; xylitol: 550 mg (±10%); mannitol; 300 mg to 700 mg (±10%); microcrystalline cellulose: 100 mg (±10%); flavoring (sufficient to produce flavor): ≈230 mg; stearic acid:. 65 mg (±10%); talc: 10 mg; and sorbitol (sufficient to make a tablet weighing 1600 mg to 2300 mg (±10%).

A preferred but non-limiting implementation of the invention is described below.

Each of the ingredients of the formulation is initially described in detail, i.e.: iron oxide, polyols, binder, lubricant, and flavoring.

1) Iron salt: the salt used is preferably a ferrous salt.

The salt can be constituted in particular by anhydrous ferrous sulfate, which is in the form of a fine greenish powder. For a dose of 10 mg of $Fe^{2+}$ per tablet, which is a typical value, the elemental iron is provided by 27.2 mg of anhydrous iron sulfate. This dose of 10 mg of $Fe^{2+}$ per tablet is naturally not limiting, and other doses could be envisaged, generally lying in the range 5 mg to 15 mg of elemental iron per tablet, although this likewise is not limiting, and corresponding to quantities of 13.6 mg to 40.8 mg of anhydrous ferrous sulfate when that is the salt used.

Other ferrous salts can be used, such as iron succinate, iron gluconate, iron glycerophosphate, iron glucoheptonate, iron dl-aspartate, iron fumarate, ferrous pyrophosphate, or ferrous oxide, and naturally on each occasion the quantity of iron salt needs to be adapted so as to obtain the desired dose of elemental iron.

In a variant, it is also possible to use ferric salts such as ferric ammonium citrate, ferric chloride, ferric citrate, ferric pyrophosphate, or ferric edetate.

2) Polyols: one of the characteristics of the formulation of the invention consists in using not less than two different polyols, preferably three polyols, that are employed as diluants, compression agents, sweeteners, and above all as agents for masking the taste of iron.

The polyols that are preferably used are sorbitol, mannitol, and xylitol.

As mentioned, these three polyols are preferably used together; if only two are used, it is preferable to associate sorbitol and xylitol, or else mannitol and xylitol.

In order to achieve the main desired effect (masking the taste of iron), one of the polyols, preferably xylitol, must on its own constitute not less than 10% and preferably not less than 20% of the total mass of the tablet, with the fraction constituted by the two or three polyols together being not less than 50% and preferably not less than 75% of the total mass.

By way of example, sorbitol can be of the Neosorb P 60 W® type from Roquette. This polyol is in the form of a granular white powder having a mean diameter of 200 µm and its possesses excellent binding properties in compression. Its sweetening power is 70% that of saccharose, it does not lead to caries, and it is low in calories (2.4 Kcal/g compared with 4 Kcal/g for saccharose).

By way of example, the mannitol can be of the Pearlitol SD 200® type, from Roquette. This polyol is in the form of a white powder that is odorless and that has a mean diameter of about 170 µm. Its sweetening power is 40% that of saccharose, it does not lead to caries, and it is also low in calories (2.4 Kcal/g).

By way of example, the xylitol can be of the Xylita 300® type from Finnsugar. This polyol is in the form of a granular crystalline white powder having a mean diameter of 250 µm. Its taste is sweat (equivalent to that of saccharose) giving an agreeable sensation of freshness in the mouth, it does not lead to caries, and it is also low in calories (2.4 Kcal/g). This particular xylitol also possesses better compressibility properties than standard xylitol. The sensation of freshness combined with the contribution of sweetness makes xylitol particularly advantageous as an agent for masking the taste of iron.

3) Binding agent: it is possible to use in particular microcrystalline cellulose, e.g. of the Avicel® type, which also makes it possible to improve the flow properties of the powder during compression.

4) Flavoring: this is selected from conventional additives as a function of the flavor to be given to the preparation; for example, it is possible to use a blackberry flavoring (SBI).

5) Lubricant: to improve manufacture, it is advantageous to use an association of lubricants, e.g. a combination of micronized stearic acid and talc. Naturally, it is possible to envisage using other lubricants that are conventional per se, e.g. magnesium stearate. The lubricant is in the form of a fine whitish powder and serves to prevent jamming in the dies of the presses when the mixture is subjected to final compression.

For manufacture, the operating protocol is as follows: the iron sulfate is premixed with the sorbitol, and the respective proportions thereof are chosen so that the volume of sorbitol is approximately double that of iron sulfate; the intermediate composition premixed in this way is then mixed with the required quantities of xylitol, mannitol, and the remaining sorbitol, together with the microcrystalline cellulose, the flavoring, and the talc; the stearic acid is then added. Finally, the mixture is compressed in a tablet press at about 15 kN to 20 kN.

A preferred general formula is as follows:

ferrous sulfate: quantity corresponding to elemental iron: 5 mg to 15 mg;

xylitol: 550 mg (±10%);

mannitol; 300 mg to 700 mg (±10%);

microcrystalline cellulose: 100 mg (±10%);

flavoring (sufficient to produce flavor):≈230 mg;

stearic acid: 65 mg (±10%):

talc: 10 mg; and sorbitol, sufficient to make a tablet weighing 1600 mg to 2300 mg (±10%).

What is claimed is:

1. A pharmaceutical medicine in unit galenical formulation of tablets for chewing or sucking and having elemental iron as its active principle, the medicine being characterized in that the dose of iron is not less than 5 mg of elemental iron per tablet and the medicine further comprises:

an iron salt;

not less than two polyols;

a binding agent;

a lubricating agent; and a flavoring agent.

2. The medicine of claim 1, in which the proportion of one of the polyols on its own is not less than 10%, of the total mass of the tablet.

3. The medicine of claim 1, in which the proportion of one of the polyols on its own is not less than 20% of the total mass of the tablet.

4. The medicine of claim 1, in which the overall proportion of polyols is not less than 50% of the total mass of the tablet.

5. The medicine of claim 1, in which the overall proportion of polyols is not less than 75% of the total mass of the tablet.

6. The medicine of claim 1, in which one of the two polyols is xylitol.

7. The medicine of claim 2 which one of the two polyols is xylitol and the proportion of xylitol is not less than 10%, of the total mass of the tablet.

8. The medicine of claims 2 in which one of the two polyols is xylitol and the proportion of xylitol is not less than 20%, of the total mass of the tablet.

9. The medicine of claim 1, having three polyols.

10. The medicine of claim 6, in which the other polyol is sorbitol and/or mannitol.

11. The medicine of claim 1, in which the binding agent is microcrystalline cellulose.

12. The medicine of claim 1, in which the lubricating agent is selected from the group consisting of micronized stearic acid, talc, and mixtures thereof.

13. The medicine of claim 1, in which the iron salt is a ferrous salt.

14. The medicine of claim 13, in which the iron salt is selected from the group consisting of iron sulfate, iron succinate, iron gluconate, iron glycerophosphate, iron glucoheptonate, iron dl-aspartate, iron fumarate, iron pyrophosphate, and iron oxide.

15. The medicine according to claim 1, in which the iron salt is a ferric salt.

16. The medicine of claim 15, in which the iron salt is selected from the group consisting of ferric ammonium citrate, ferric chloride, ferric citrate, ferric pyrophosphate, and ferric edetate.

17. The medicine of claim 1, in which the dose of iron is not less than 10 mg to 40 mg of elemental iron per tablet.

18. The medicine of claim 1, having the following general formula:

ferrous sulfate: quantity corresponding to elemental iron: 5 mg to 15 mg;

xylitol: 495 mg to 605 mg;

mannitol; 270 mg to 770 mg;

microcrystalline cellulose: 90 mg to 110 mg;

flavoring (sufficient to produce flavor): ≈230 mg;

stearic acid: 58.5 mg to 71.5 mg;

talc: 10 mg; and sorbitol (sufficient to make a tablet weighing 1440 mg to 2530 mg).

19. A pharmaceutical medicine in unit galenical formulation of tablets for chewing or sucking and having elemental iron as its active principle, the medicine being characterized in that it further comprises:

an iron salt;

not less than two polyols;

a binding agent;

a lubricating agent; and a flavoring agent;

and has the following general formula:

ferrous sulfate: quantity corresponding to elemental iron: 5 mg to 15 mg;

xylitol: 495 mg to 605 mg;

mannitol; 270 mg to 770 mg;

microcrystalline cellulose: 90 mg to 110 mg;

flavoring (sufficient to produce flavor): ≈230 mg;

stearic acid: 58.5 mg to 71.5 mg;

talc: 10 mg; and sorbitol (sufficient to make a tablet weighing 1440 mg to 2530 mg).

* * * * *